United States Patent
Sawyer et al.

(10) Patent No.: US 8,067,634 B2
(45) Date of Patent: Nov. 29, 2011

(54) PROCESS FOR PRODUCING ALLYL ACETATE

(75) Inventors: Gary A. Sawyer, Media, PA (US);
Shaw-Chan Lin, West Chester, PA (US);
Elizabeth I. Ross-Medgaarden, West Grove, PA (US); Andrew P. Kahn, Eagleville, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 207 days.

(21) Appl. No.: 12/589,933

(22) Filed: Oct. 30, 2009

(65) Prior Publication Data
US 2011/0105792 A1    May 5, 2011

(51) Int. Cl.
*C07C 67/02* (2006.01)

(52) U.S. Cl. .................................................. 560/261
(58) Field of Classification Search .................. None
See application file for complete search history.

(56) References Cited

U.S. PATENT DOCUMENTS

| | | | |
|---|---|---|---|
| 3,925,452 A * | 12/1975 | Swodenk et al. | 560/245 |
| 3,965,152 A * | 6/1976 | Smith et al. | 560/234 |
| 3,970,713 A | 7/1976 | Scharfe et al. | |
| 5,011,980 A * | 4/1991 | Sano et al. | 560/245 |
| 6,303,536 B1 | 10/2001 | Chen et al. | |
| 2006/0167307 A1 | 7/2006 | Saihata et al. | |
| 2006/0247462 A1 | 11/2006 | Saihata et al. | |

* cited by examiner

*Primary Examiner* — Karl J Puttlitz

(57) ABSTRACT

A process for producing allyl acetate is disclosed. The process comprises reacting propylene, acetic acid, and oxygen in the presence of a supported palladium catalyst in an adiabatic reactor.

13 Claims, 3 Drawing Sheets

PROCESS FOR PRODUCING ALLYL ACETATE

FIELD OF THE INVENTION

This invention relates to a process for producing allyl acetate from propylene, acetic acid, and oxygen in the presence of a supported palladium catalyst in an adiabatic reactor.

BACKGROUND OF THE INVENTION

Oxidation of propylene in the presence of acetic acid catalyzed by a palladium catalyst to produce allyl acetate is known. The process includes a reaction (acetoxylation) of propylene with oxygen and acetic acid to form a mixture comprising allyl acetate, propylene, oxygen, acetic acid, water, carbon dioxide, and possibly other inert gases. The reaction mixture is typically separated into a gas stream comprising propylene, oxygen, acetic acid, water, and carbon dioxide, and a liquid stream comprising allyl acetate, acetic acid, and water. Allyl acetate can be separated from the liquid stream. At least a portion of the acetic acid and water separated from the liquid stream is recycled to the acetoxylation reaction.

In addition to allyl acetate, the reaction generally also gives carbon dioxide, allyl diacetate, and possibly acrolein and propionaldehyde. The heat of reaction for the formation of allyl acetate from propylene, acetic acid, and oxygen is about −37.9 kcal/mole. As the reaction is highly exothermic, generally multitubular reactors are used. For example, U.S. Pat. No. 3,970,713 teaches a multitubular reactor containing reactor tubes having a length of from 4 to 8 meters and an internal diameter of from 20 to 50 mm. In a typical mulitubular reactor, the catalyst is arranged in the reactor tubes. A heat carrier fluid circulates externally around the reactor tubes to remove the heat generated by the reaction. Mulitubular reactors are suitable for those reactions with a large heat of reaction as well as reactions that are extremely temperature-sensitive. A mulitubular reactor is often called an "isothermal reactor" because of its relatively uniform temperature through the reactor. Usually, the temperature variation through a multitubular reactor is small, generally less than 20° C.

The disadvantage of a multitubular reactor is its high equipment cost. In addition, it can be time consuming to load and unload hundreds, often thousands, of reactor tubes. It is particularly difficult to remove used catalyst from the reactor tubes when the catalyst in the tubes has agglomerated or fused.

SUMMARY OF THE INVENTION

This invention is a process for producing allyl acetate. The process comprises reacting a feed comprising propylene, acetic acid, and oxygen in the presence of a supported palladium catalyst in an adiabatic fixed-bed reactor.

DETAILED DESCRIPTION OF THE INVENTION

Figure 2:
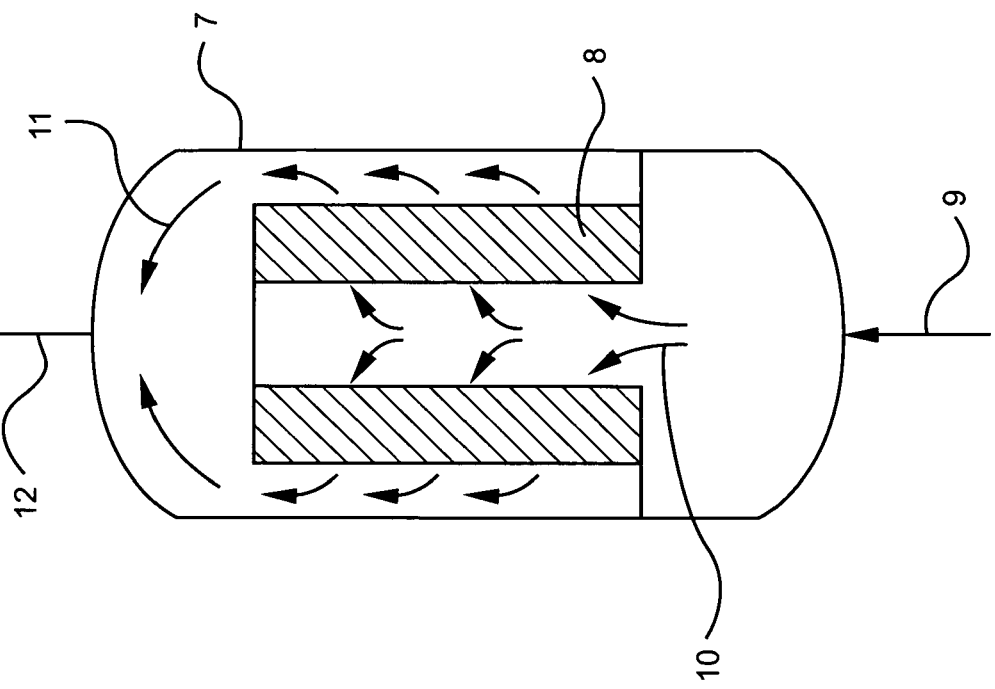
FIG. 2 is a schematic representation of a radial-flow adiabatic reactor.

The process comprises reacting a feed comprising propylene, acetic acid, and oxygen in the presence of a supported palladium catalyst in an adiabatic fixed-bed reactor.

The process uses a supported palladium catalyst. The amount of palladium is 0.1 to 5.0 weight percent (wt %), preferably 0.3 to 1.5 wt % of the supported catalyst.

The catalyst may comprise a Group 11 element, i.e., gold, copper, silver, and mixtures thereof. The content of gold, copper, or silver may be in the range of 0 to 5.0 wt %, preferably in the range of 0.02 to 1.0 wt % of the supported catalyst.

The catalyst may additionally comprise an activator. An activator is an alkali or alkaline earth metal compound, examples of which are hydroxides, acetates, nitrates, carbonates, and bicarbonates of potassium, sodium, cesium, magnesium, barium, and the like. Potassium and cesium salts are preferred activators. The activator content may be in the range of 0 to 15 wt %, preferably 1.5 to 10 wt % of the supported catalyst.

The supported palladium catalyst comprises a carrier. Suitable carriers include alumina, silica, titania, carbon, and the like, and mixtures thereof. Preferably, the carrier has a surface area of at least 1 $m^2/g$ and a pore volume of 0.1 to 1.5 mL/g.

The catalyst may be prepared by many techniques. Examples of these techniques are disclosed in U.S. Pat. Nos. 3,925,452, 5,011,980, 6,303,536, and U.S. Pat. Appl. Pub. Nos. 2006/0167307 and 2006/0247462.

In preparing the catalyst, the carrier can be simultaneously or successively impregnated with a palladium compound, optionally a Group 11 metal salt, and optionally an activator. Preferably, the impregnation is performed in aqueous solutions.

Suitable palladium compounds include palladium chloride, sodium chloropalladate, palladium nitrate, palladium sulfate, the like, and mixtures thereof. Suitable Group 11 metal salts include chlorides, nitrates, sulfates. Examples are tetrachloroauric acid, sodium tetrachloroaurate, copper chloride, copper nitrate, copper sulfate, silver nitrate, the like, and mixtures thereof. Suitable activators include hydroxides, carbonates, bicarbonates, metasilicates of alkali and alkaline earth metals, the like, and mixtures thereof.

One method to impregnate the carrier involves contacting the carrier with an aqueous solution containing both a palladium compound and a Group 11 metal salt. In another method, the carrier is contacted with a palladium compound and a Group 11 metal salt in separate steps.

A fixing agent may be used in preparing the catalyst. Fixing agents help to bind the palladium compound and the Group 11 metal salts, if used, to the carrier. Suitable fixing agents include alkali metal, alkaline earth metal, or ammonium compounds, for example, their hydroxides, carbonates, bicarbonates, metasilicates, and the like, and mixtures thereof. A fixing agent may be contacted with the carrier during or after the carrier is impregnated with the palladium compound and optionally the Group 11 metal salt.

The impregnated carrier is usually calcined (heated at an elevated temperature) in a non-reducing atmosphere. Preferably, the calcination is carried out at a temperature in the range of 100 to 600° C., more preferably, in the range of 250 to 500° C. Suitable non-reducing gases for the calcination include helium, nitrogen, argon, oxygen, air, carbon dioxide, the like, and mixtures thereof. Preferably, the calcination is carried out in nitrogen, oxygen, air, or mixtures thereof.

Following the calcination, the resulting material is normally reduced to convert at least a portion of the palladium and the Group 11 metal, if used, to the corresponding elements with zero valence. The reduction is performed by contacting it with a reducing agent. Suitable reducing agents include hydrogen, carbon monoxide, olefins, aldehydes, alcohols, hydrazines, the like, and mixtures thereof. Temperatures employed for the reduction is in the range of 20 to 700° C.

Hydrogen gas is a preferred reducing agent. Generally, a gas mixture containing hydrogen and another gas such as argon, helium, nitrogen, or the like, is used. The reduction temperature is preferably in the range of 300 to 700° C., more preferably, in the range of 450 to 550° C.

The feed comprises propylene. The concentration of propylene in the feed is generally between 20 to 80 mol %, preferably 40 to 70 mol %. The feed to the reactor includes all streams entering the reactor. A propylene content of greater than 50 mol % is particularly desirable. Commercially available polymer grade propylene and chemical grade propylene are suitable sources of propylene. The source of propylene preferably has a purity of at least 90 mol %, most preferably, at least 99.5 mol %.

The feed comprises acetic acid. The concentration of acetic acid in the feed typically is 8 to 20 mol %, preferably 10 to 18 mol %.

The feed comprises oxygen. The concentration of oxygen in the feed is typically 2 to 8 mol %, preferably 3 to 6 mol %. The oxygen may be supplied to the process in the form of a mixture with an inert gas such as nitrogen. Air may be used. The oxygen source used for the process preferably has a purity of at least 90 mol %, more preferably at least 95 mol %. The allowed oxygen concentration in the feed is determined by the flammability limit. The flammability limit of the feed depends on the temperature, the pressure, and its composition.

The feed may comprise a diluent. A diluent helps to prevent formation of an explosive mixture in the reactor and control the temperature rise. Examples of suitable diluents include propane, nitrogen, helium, argon, the like, and mixtures thereof.

The feed may comprise carbon dioxide. Carbon dioxide improves the selectivity to allyl acetate and suppresses the formation of carbon dioxide. See copending U.S. patent application Ser. No. 12/586,966, filed Sep. 30, 2009. Preferably the feed comprises greater than 1 mol % carbon dioxide.

The feed may comprise water. The concentration of water vapor in the feed is typically from 0 to 5 mol %, more preferably from 1 to 4 mol %.

The feed is gaseous under the reaction conditions. Accordingly, the quantities of acetic acid and water entering the reactor are adjusted so that the feed is in gas phase under the temperature and pressure selected for the reaction.

Figure 1:
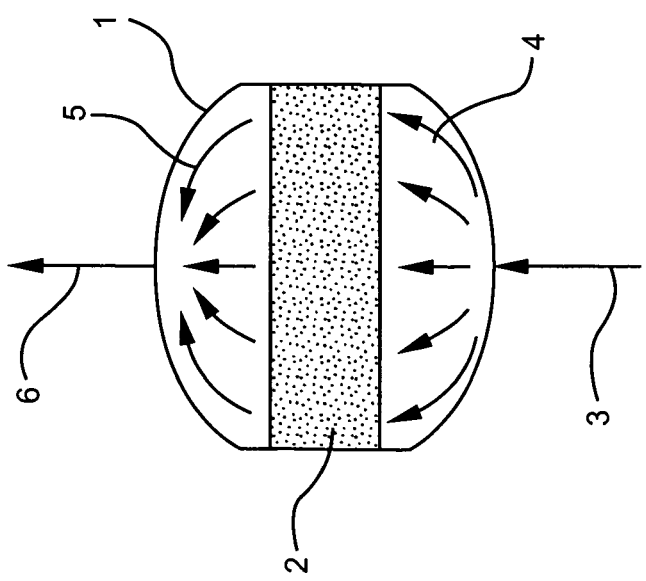
FIG. 1 is a schematic representation of a cylindrical adiabatic reactor.

The reaction is performed in an adiabatic fixed-bed reactor. In an adiabatic reactor, the bed temperature rises due to the heat of the reaction and the heat is not removed from the reactor directly. One commonly used reactor is cylindrical, as shown in FIG. 1. In FIG. 1, a stream enters reactor 1 containing catalyst bed 2, and exits the reactor via line 6. An axial-radial flow reactor, as shown in FIG. 2, may also be used. In an axial-radial flow reactor, the catalyst bed is located in a space between two concentric screen rings or perforated plate rings, and is traversed radially, either from the inside to the outside or from the outside to the inside. In FIG. 2, a stream enters reactor 7 via line 9, passes a ring-shaped catalyst bed 8 as shown by arrows 10 and 11, and exits the reactor via line 12. A stream can also enter the reactor from its top and exits from its bottom.

The propylene conversion is generally controlled so that the temperature rise in the reactor is not excessive, for example, less than 80° C. Propylene conversion in the reactor is generally 2 to 10%.

The reaction is generally performed at a temperature in the range of 100 to 250° C., preferably 125 to 200° C. In an adiabatic reactor, temperature can be lowered by lowering the temperature of the reactor inlet stream. Generally, the reaction pressure is in the range of 15 to 450 psia, preferably in the range of 30 to 150 psia.

The reaction is preferably conducted in two or more adiabatic reactors in series. There are many advantages of using two or more reactors in series instead of one single reactor. First, the temperature rise in each reactor is reduced. Second, cooling can be provided between reactors. Third, a reactant may be added to an individual reactor so that the composition of the stream entering each reactor can be adjusted. In one preferred process, each adiabatic reactor has at least one heat exchanger located between it and the other adiabatic reactors. For example, in a three reactor in series system, while fresh propylene is fed to the first reactor, it is preferred to feed a portion (e.g., approximately one third) of fresh oxygen supplied to the process to each reactor to reduce the oxygen concentration in each reactor and improve the selectivity to allyl acetate for the process.

The reaction is generally operated at a space velocity in the range of 10 to 15,000 $h^{-1}$, more preferably in the range of 300 to 8,000 $h^{-1}$.

The reaction produces a mixture comprising allyl acetate, propylene, oxygen, acetic acid, water, carbon dioxide, and inert gases if used. Typically, the reaction mixture is partially condensed or contacted with a cooled liquid such as acetic acid and water to form a liquid stream which can be separated from a remaining gas stream. The liquid stream typically contains 5 to 20 wt % allyl acetate, the remainder being a mixture of acetic acid and water. Depending upon the concentrations of components, the liquid stream may be separated into an organic stream comprising allyl acetate, and an aqueous stream comprising water and acetic acid. Preferably, the aqueous stream or a portion of it is recycled to the reaction.

The gas stream can be compressed and recycled. There are various techniques to recycle the gas stream. In one example, a recycle gas is passed through an evaporator containing acetic acid and water so that the recycle gas is charged with the requisite quantity of acetic acid and water from the evaporator before it enters the reactor. Thus, the feed contains not only fresh reactants supplier to the process, but also the recycled streams from the process.

Example 1

Figure 3:
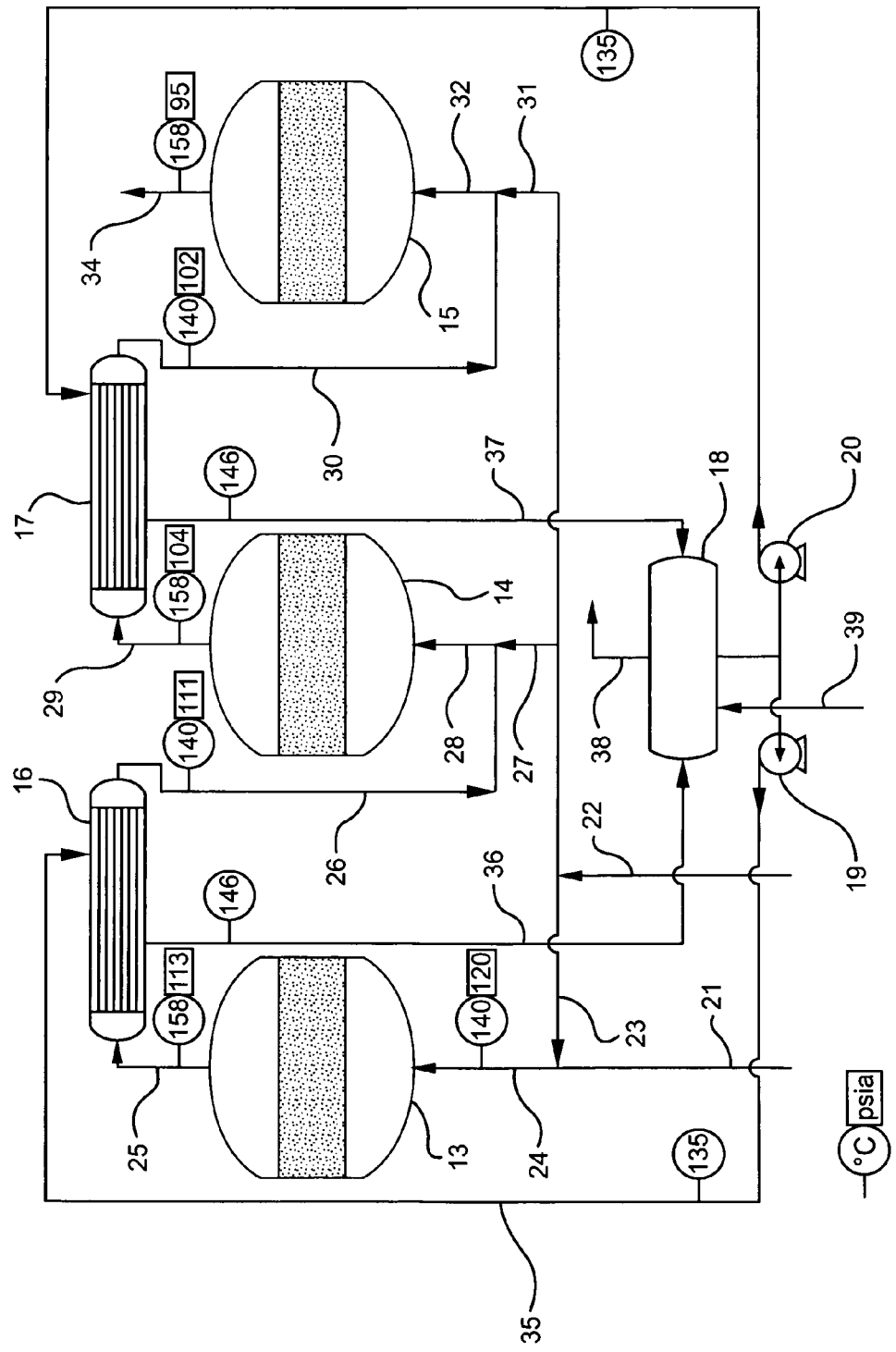
FIG. 3 shows three adiabatic reactors in series for allyl acetate production.

The reactor section designed for an allyl acetate plant with an annual capacity of $255 \times 10^3$ metric ton is shown in FIG. 3. In FIG. 3, the temperature and the pressure of each stream are displayed by numbers in a circle and a rectangle. Reactors 13, 14, 15 each contain a supported palladium catalyst bed 20 ft in diameter and 6 ft in height. Fresh oxygen (99.99%) enters the process via line 22, which is divided into three equal portions in lines 23, 27, and 31. A stream containing propylene, propane, allyl acetate, water, oxygen, acetic acid, argon, and carbon dioxide in line 21 is mixed with oxygen from line 23, and fed to reactor 13 via line 24 at 140° C. and 120 psia. The feed include propylene, acetic acid, and oxygen freshly supplied to reactor and recycles streams from the process. Small amount of allyl acetate is present in the recycled stream. The reaction is performed at 120 psia. The effluent from reactor 13 is cooled by heat exchanger 16 to 140° C., mixed with oxygen from line 27, and enters reactor 14 via line 28. The effluent from reactor 14 is cooled by heat exchanger 17, mixed with oxygen from line 31, and fed to reactor 15 via line 32. The effluent from the reactor 15 is processed in a down-stream separation/purification section (not shown). The reactor material balance is shown in Table 1. The selectivity to allyl acetate from propylene is assumed to be 98%. The catalyst productivity is assumed to be 200 gram allyl acetate per liter per hour (copending U.S. patent application Ser. No. 12/586,966, filed Sep. 30, 2009). The feed to each reactor contains 58 mol % propylene. Propylene conversion in each reactor is 4%.

Boiler feed water, at 135° C., is fed to heat exchanger 16 and exits the heat exchanger via line 36 at 146° C.; similarly for heat exchanger 17. Heated boiler feed water from lines 36 and 37 are used to generate 30 psia steam at a rate of 29,700 lb per hour by flash boiler 18. Additional water is supplemented to the reboiler via line 39.

Comparative Example 2

Figure 4:
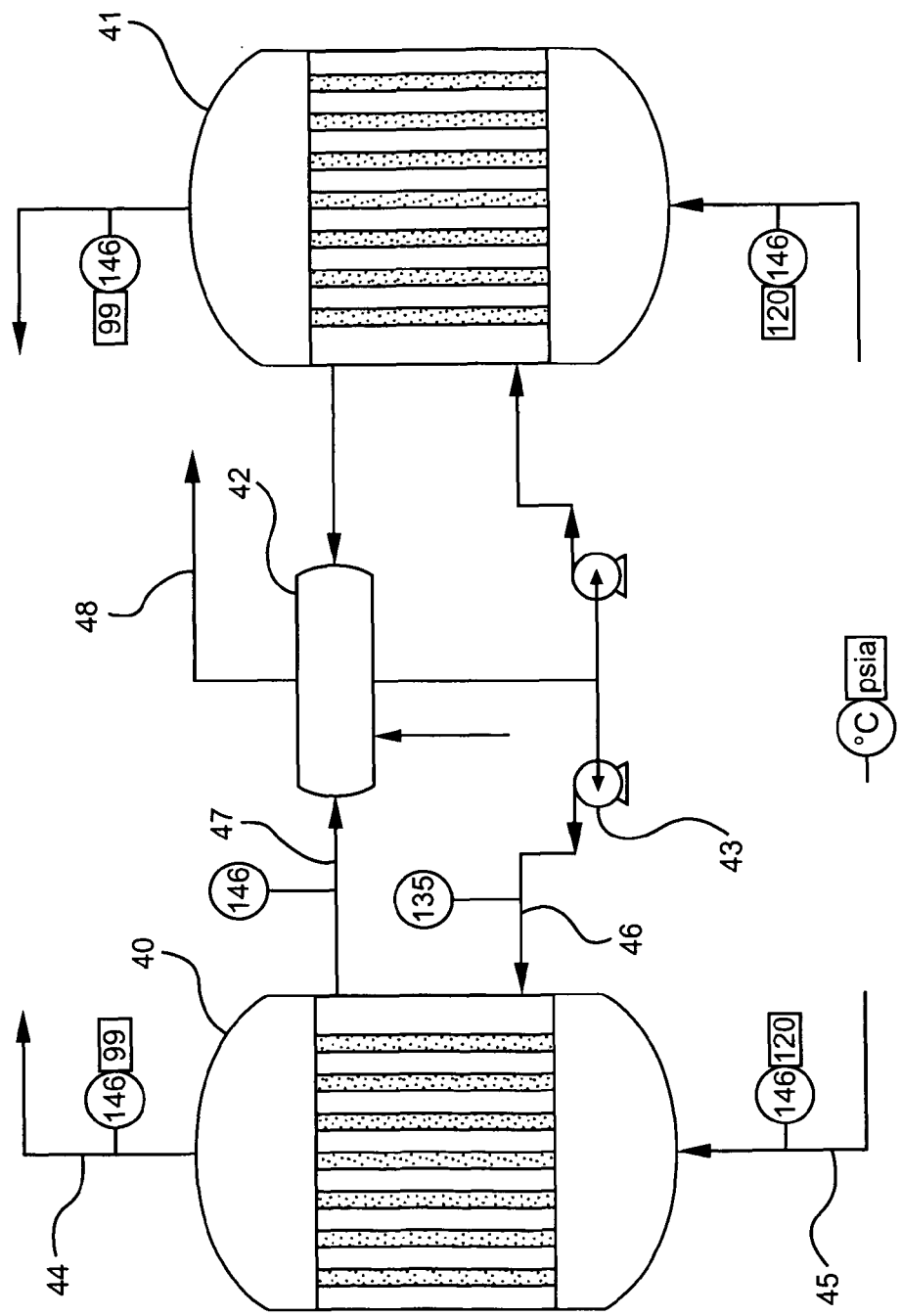
FIG. 4 shows two parallel multitubular reactors for allyl acetate production.

The reactor section designed for an allyl acetate plant using multitubular reactors with an annual capacity of 255×10³ metric ton is shown in FIG. 4. Two multitubular reactors are used in parallel to keep their sizes practical. Each reactor shell has a diameter of 24 ft. Each reactor contains 28920 reactor tubes having an internal diameter of 1 inch and a height of 18 ft. A feed enters reactor 40 via line 45 from the bottom of the reactor and passes through packed tubes and exits the reactor via line 44 at 145° C. and at a pressure of 99 psia. The effluent from the reactor 40 is processed in a down-stream separation/purification section (not shown). The selectivity to allyl acetate from propylene and the catalyst productivity are assumed to be the same as in Example 1. The feed to reactor 40 contains 58 mol % propylene. Propylene conversion is 4%. The combined reactor material balance for two reactors is shown in Table 2.

Heat of the reaction is removed by a circulating boiler feed water. Cooling water is fed to the reactor shell space via line 46, exits via line 47, and is fed to flash boiler 42, generating 44,180 lb/h low pressure steam. Reactor 41 is operated in parallel in the same fashion as reactor 40. Reactor effluents from reactors 40 and 41 are passed to a separation/purification section of the plant (not shown).

It is estimated that the total cost of reactors and heat exchangers in Example 1 is about ⅙ of the cost in Example 2. Example 1 represents significant savings in total equipment costs. In addition, it also allows splitting fresh oxygen supplied to the process, thus lowering the average oxygen concentration across the reactor for safer operation. The average oxygen concentration from inlet to outlet is 1.5 wt % in Example 1 as compared to 1.7 wt % in Example 2.

TABLE 1

|  | 1st Reactor Feed (kg/h) | 2nd Reactor Feed (kg/h) | 3rd Reactor Feed (kg/h) | 3rd Reactor Outlet (kg/h) |
| --- | --- | --- | --- | --- |
| Argon | 14585 | 14585 | 14585 | 14585 |
| Oxygen | 9399 | 9399 | 9399 | 7633 |
| Carbon Dioxide | 112681 | 112750 | 112819 | 112887 |
| Propylene | 328832 | 324448 | 320064 | 315679 |
| Propane | 7506 | 7506 | 7506 | 7506 |
| Allyl Acetate | 309 | 10532 | 20754 | 30977 |
| Water | 2427 | 4332 | 6237 | 8143 |
| Acetic Acid | 121363 | 115169 | 108975 | 102780 |
| Other | 1 | 150 | 299 | 448 |
| Total | 597105 | 598872 | 600639 | 600639 |

TABLE 2

|  | Reactor Feed (kg/h) | Reactor Outlet (kg/h) |
| --- | --- | --- |
| Argon | 14585 | 14585 |
| Oxygen | 12933 | 7633 |
| Carbon Dioxide | 112681 | 112887 |
| Propylene | 328832 | 315679 |
| Propane | 7506 | 7506 |
| Allyl Acetate | 309 | 30977 |
| Water | 2427 | 8143 |
| Acetic Acid | 121363 | 102780 |
| Other | 1 | 448 |
| Total | 600639 | 600639 |

We claim:

1. A process for producing allyl acetate, comprising reacting a feed comprising propylene, acetic acid, and oxygen in the presence of a supported palladium catalyst in an adiabatic fixed-bed reactor.

2. The process of claim 1 wherein the reaction gives at least 95 mol % selectivity to allyl acetate from propylene.

3. The process of claim 1 wherein the reaction gives at least 98 mol % selectivity to allyl acetate from propylene.

4. The process of claim 1 wherein the reaction is conducted at a temperature in the range of 250 to 400° C.

5. The process of claim 1 wherein the feed comprises greater than 50 mol % propylene.

6. The process of claim 1 wherein the feed comprises 3 to 6 mol % oxygen.

7. The process of claim 1 wherein the feed comprises a diluent selected from the group consisting of propane, argon, nitrogen, and mixtures thereof.

8. The process of claim 1 wherein the feed comprises greater than 1 mol % carbon dioxide.

9. The process of claim 1 wherein the reaction is conducted in two or more adiabatic reactors in series.

10. The process of claim 9 wherein each reactor has at least one heat exchanger between it and the other reactors.

11. The process of claim 9 wherein a portion of the oxygen supplied to the reaction is fed to each reactor.

12. The process of claim 1 wherein the reaction is conducted in three reactors in series and each reactor has at least one heat exchanger between it and the other reactors.

13. The process of claim 12 wherein a portion of the oxygen supplied to the process is fed to each reactor.

* * * * *